United States Patent
Hamamoto

(10) Patent No.: US 11,510,882 B2
(45) Date of Patent: Nov. 29, 2022

(54) NON-READHERABLE ADHESIVE PATCH

(71) Applicant: MEDRX CO., LTD., Higashikagawa (JP)

(72) Inventor: Hidetoshi Hamamoto, Higashikagawa (JP)

(73) Assignee: MEDRX CO., LTD., Kagawa (JP)

(*) Notice: Subject to any disclaimer, the term of this patent is extended or adjusted under 35 U.S.C. 154(b) by 0 days.

(21) Appl. No.: 16/481,041

(22) PCT Filed: Sep. 21, 2018

(86) PCT No.: PCT/JP2018/035191
§ 371 (c)(1),
(2) Date: Jul. 25, 2019

(87) PCT Pub. No.: WO2019/059377
PCT Pub. Date: Mar. 28, 2019

(65) Prior Publication Data
US 2020/0214992 A1    Jul. 9, 2020

(30) Foreign Application Priority Data
Sep. 22, 2017  (JP) ............................. JP2017-183086

(51) Int. Cl.
*A61K 9/70* (2006.01)
*A61K 31/4468* (2006.01)
*A61K 31/485* (2006.01)

(52) U.S. Cl.
CPC ........ *A61K 9/7061* (2013.01); *A61K 31/4468* (2013.01); *A61K 31/485* (2013.01)

(58) Field of Classification Search
CPC ... A61K 31/4468; A61K 47/10; A61K 9/7061
See application file for complete search history.

(56) References Cited

U.S. PATENT DOCUMENTS

| | | | | |
|---|---|---|---|---|
| 5,505,956 A | * | 4/1996 | Kim | A61K 9/7076 424/448 |
| 2002/0010127 A1 | * | 1/2002 | Oshlack | A61K 9/2054 514/282 |
| 2002/0100185 A1 | * | 8/2002 | Sitz | F26B 25/006 34/427 |
| 2008/0292684 A1 | | 11/2008 | Colombo et al. | |
| 2018/0140610 A1 | * | 5/2018 | Yacoby-Zeevi | A61K 47/22 |

FOREIGN PATENT DOCUMENTS

| | | | | |
|---|---|---|---|---|
| EP | 3081211 | | 10/2016 | |
| EP | 3434267 A1 | | 1/2019 | |
| JP | 9-169635 A | | 6/1997 | |
| JP | H09169635 A | * | 6/1997 | ........... A61K 31/415 |
| JP | 2006-22057 A | | 1/2006 | |
| JP | 2006022057 A | * | 1/2006 | ............. A61K 47/10 |
| JP | 2010-229045 A | | 10/2010 | |
| JP | 2010229045 A | * | 10/2010 | ............. A61K 31/13 |
| JP | 2014-24764 A | | 2/2014 | |
| JP | 2016-179949 A | | 10/2016 | |
| JP | 2016179949 A | * | 10/2016 | |
| JP | 2017-196878 | | 11/2017 | |
| WO | WO 2003/103673 | | 6/2003 | |
| WO | WO 2005/072669 A1 | | 8/2005 | |
| WO | WO-2005123046 A1 | * | 12/2005 | ........... A61K 9/7061 |
| WO | WO 2006/082728 A1 | | 8/2006 | |
| WO | WO-2006082728 A1 | * | 8/2006 | ............. A61P 25/28 |
| WO | WO 2005/072669 | | 9/2007 | |
| WO | WO 2006/082728 | | 6/2008 | |
| WO | 2016/009063 A1 | | 1/2016 | |
| WO | WO 2015/087927 | | 3/2017 | |

OTHER PUBLICATIONS

Machine translation of JP-2016179949, pp. 1-20 (Year: 2016).*
Buddrick, O. et al. "Heptane as a less toxic option than hexane for the separation of vitamin E from food products using normal phase HPLC" RSC Adv., 2013, 3, 24063 (Year: 2013).*
International Search Report received in International Patent Application No. PCT/JP2018/035191 dated Dec. 18, 2018.
Extended European Search Report issued in corresponding European Patent Application No. 18857629.2 dated Jun. 4, 2021.

* cited by examiner

*Primary Examiner* — Andrew S Rosenthal
(74) *Attorney, Agent, or Firm* — Morgan, Lewis & Bockius LLP

(57) ABSTRACT

A patch preparation which can produce the effect for preventing any problems due to the misuse of the patch preparation, includes a support and a plaster wherein the plaster includes a) an aliphatic compound with hydrophilic group which is in solid state at room temperature, b) a non-aqueous adhesive, and c) a solvent with a vapor pressure of 1 kPa or more at 20° C.

22 Claims, 1 Drawing Sheet

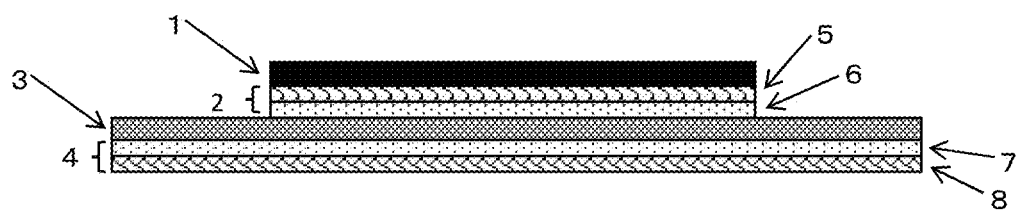

NON-READHERABLE ADHESIVE PATCH

CROSS-REFERENCES TO RELATED APPLICATIONS

This patent application claims the benefit of Japanese Patent Application No. 2017-183086 filed on Sep. 22, 2017. The contents of this application are hereby incorporated by this reference in its entirety.

TECHNICAL FIELD

The present invention relates to a patch preparation with no re-adhesive effect.

BACKGROUND ART

Accidents due to the misuse of a patch preparation have recently increased. The conventional drug for such patch preparation was typically a local drug and a non-inflammatory drug with relatively low physiological activity. On the other hand, a patch preparation comprising a systemic drug and/or a drug with high physiological activity as the active ingredient is also increasing. The misuse of such patch preparation may cause serious poisoning. Even if such patch preparation is used at a defined dose, a certain amount of the drug remains in the patch preparation. Some poisoning accidents may be caused by the misuse of such patch preparation. In particular, some serious accidents are sometimes caused by the application of the patch preparation after being used by an adult to a toddler. Hence, the development of a patch preparation for preventing the risk of such accidents due to the misuse of the patch preparation has been desired. In order to prevent such problems, some techniques to properly discard a patch preparation after use have been suggested (e.g., Patent Document 1). Also, Patent Document 2 discloses a patch preparation which renders an opioid ineffective when the patch preparation is dissolved for the opioid abuse by incorporating an antagonist into the intermediate layer of the preparation.

In addition, Patent Document 3 discloses a patch preparation comprising a cover material which comprises an adhesive layer for covering a drug reservoir layer as a multi-layered patch preparation.

PRIOR ART DOCUMENTS

Patent Documents

Patent Document 1: WO 2003/103673
Patent Document 2: JP 2017-19878
Patent Document 3: WO 2015/87927

SUMMARY OF INVENTION

Problem to be Solved by the Invention

An object of the present invention is to provide a patch preparation which can produce the effect for preventing any problems such as accidents due to the misuse of the patch preparation. That is, the object of the present invention is to provide a patch preparation which makes it difficult or impossible to re-apply the patch preparation to the skin after use.

Means for Solving the Problems

The present inventors have studied a patch preparation with no re-adhesive effect, and then have found that the addition of an aliphatic compound with hydrophilic group which is in solid state at room temperature, a non-aqueous adhesive, and a solvent with a specific vapor pressure into the plaster of a patch preparation reduces the adhesibility of the patch preparation after use and makes it difficult or impossible to re-apply the patch preparation to the skin. The present inventors have then completed the present invention on the basis of the above findings.

That is, the present invention provides the following embodiments (1)-(5).

(1) A patch preparation comprising a support and a plaster, wherein the plaster comprises an aliphatic compound with hydrophilic group which is in solid state at room temperature, a non-aqueous adhesive, and a solvent with a vapor pressure of 1 kPa or more at 20° C. in an amount of 2-15% by weight.
(2) The patch preparation of the above (1), wherein the support is impermeable to the solvent.
(3) The patch preparation of the above (1), wherein the support is permeable to the solvent.
(4) The patch preparation of any one of the above (1)-(3), wherein the plaster further comprises a drug.
(5) A patch preparation in which a first support, a first plaster, a second support, and a second plaster are sequentially laminated, wherein the first and second plasters comprise a solvent with a vapor pressure of 1 kPa or more at 20° C. in an amount of 2-35% by weight, the second support is impermeable to the solvent, the surface areas of the first plaster, the second support, and the second plaster satisfy the following formula: first plaster>second support≥second plaster, and the second plaster comprises a drug.

More specifically, the present invention provides the following embodiments (1')-(28').

(1') A patch preparation comprising a support and a plaster, wherein the plaster comprises a) an aliphatic compound with hydrophilic group which is in solid state at room temperature; b) a non-aqueous adhesive; and c) a solvent with a vapor pressure of 1 kPa or more at 20° C.
(2') The patch preparation of (1'), wherein the support is a solvent-impermeable support.
(3') The patch preparation of (1'), wherein the support is a solvent-permeable support.
(4') The patch preparation of any one of (1')-(3'), wherein the aliphatic compound is a compound with a melting point of 50-80° C.
(5') The patch preparation of any one of (1')-(4'), wherein the aliphatic compound is one or more selected from the group consisting of $C_{8-22}$ higher alcohol and $C_{8-22}$ higher fatty acid.
(6') The patch preparation of any one of (1')-(5'), wherein the aliphatic compound is one or more selected from the group consisting of stearyl alcohol, cetyl alcohol, cetostearyl alcohol, myristic acid, palmitic acid, and stearic acid.
(7') The patch preparation of any one of (1')-(6'), wherein the amount of the aliphatic compound is 1-30% by weight relative to the total weight of the plaster.
(8') The patch preparation of any one of (1')-(7'), wherein the non-aqueous adhesive comprises a mass base.
(9') The patch preparation of (8'), wherein the mass base is one or more selected from the group consisting of an acrylic polymer, a rubber polymer, and a silicone polymer.
(10') The patch preparation of (8') or (9'), wherein the mass base is an acrylic polymer or a combination of an acrylic polymer and a rubber polymer.
(11') The patch preparation of any one of (1')-(10'), wherein the amount of the non-aqueous adhesive is 40-90% by weight relative to the total weight of the plaster.

(12') The patch preparation of any one of (1')-(11'), wherein the solvent is one or more selected from the group consisting of an acyclic or cyclic aliphatic hydrocarbon, an aliphatic monoalcohol, an ester, and water.
(13') The patch preparation of any one of (1')-(12'), wherein the solvent is one or more selected from the group consisting of an acyclic or cyclic aliphatic hydrocarbon, an ester, and water.
(14') The patch preparation of any one of (1')-(13'), wherein the solvent is ethyl acetate, n-heptane, or a combination thereof.
(15') The patch preparation of any one of (1')-(14'), wherein the amount of the solvent is 2-35% by weight.
(16') The patch preparation of any one of (1')-(14'), wherein the amount of the solvent is 2-15% by weight.
(17') The patch preparation of any one of (1')-(16'), wherein the plaster further comprises a drug.
(18') The patch preparation of (17'), wherein the drug is an opioid analgesic agent.
(19') The patch preparation of (18'), wherein the opioid analgesic agent is oxycodone or fentanyl.
(20') A multi-layered patch preparation comprising a first support, a first plaster, a second support, and a second plaster, wherein the first plaster is disposed on the first support, the second support is disposed on the first plaster, and the second plaster is disposed on the second support; the surface areas of the first plaster, the second support, and the second plaster satisfy the following formula:

first plaster>second support≥second plaster; and the first plaster comprises a solvent with a vapor pressure of 1 kPa or more at 20° C., and the second plaster comprises a drug.
(21') A multi-layered patch preparation comprising a first support, a first plaster, a second support, and a second plaster, wherein the first plaster is disposed on the first support, the second support is disposed on the first plaster, and the second plaster is disposed on the second support; the surface areas of the first plaster, the second support, and the second plaster satisfy the following formula:

first plaster>second support≥second plaster; and the second support is a solvent-impermeable support, and the second plaster comprises a drug.
(22') A multi-layered patch preparation comprising a first support, a first plaster, a second support, and a second plaster, wherein the first plaster is disposed on the first support, the second support is disposed on the first plaster, and the second plaster is disposed on the second support; the surface areas of the first plaster, the second support, and the second plaster satisfy the following formula:

first plaster>second support≥second plaster; and the second support is a solvent-impermeable support, the first plaster comprises a solvent with a vapor pressure of 1 kPa or more at 20° C., and the second plaster comprises a solvent with a vapor pressure of 1 kPa or more at 20° C. and a drug.
(23') The patch preparation of any one of (20')-(22'), wherein the first support is a solvent-impermeable support.
(24') The patch preparation of (23'), wherein the solvent-impermeable support is non-woven cloth laminated film.
(25') The patch preparation of (23'), wherein the film moiety of the non-woven cloth laminated film is disposed on the first support.
(26') The patch preparation of any one of (20')-(25'), wherein the second support is non-woven cloth laminated film.
(27') The patch preparation of (26'), wherein the non-woven cloth moiety of the non-woven cloth laminated film is disposed on the second support.

(28') The patch preparation of any one of (20')-(27'), wherein the amount of the solvent is 2-35% by weight.

Each feature of the above (1') to (28') may be optionally selected and combined two or more.

BRIEF DESCRIPTION OF THE DRAWINGS

FIG. 1 shows the cross-sectional view of the multi-layered structure comprising a support and a plaster. 1 shows the second plaster comprising a drug, 2 shows the second support which is non-woven cloth laminated film, 3 shows the first plaster which is an adhesive layer, and 4 shows the first support which is non-woven cloth laminated film. In addition, 5 shows the non-woven cloth moiety of the second support, 6 shows the film moiety of the second support, 7 shows the film moiety of the first support, and 8 shows the non-woven cloth moiety of the first support.

DETAILED DESCRIPTION OF THE PREFERRED EMBODIMENTS

The patch preparation of the present invention comprises a support and a plaster, and the plaster comprises an aliphatic compound with hydrophilic group which is in solid state at room temperature, a non-aqueous adhesive, and a solvent with a vapor pressure of 1 kPa or more (e.g. 1-60 kPa) at 20° C.

[Aliphatic Compound with Hydrophilic Group which is in Solid State at Room Temperature]

The aliphatic compound as used herein is an aliphatic compound with hydrophilic group which is in solid state at room temperature. The aliphatic compound is preferably an aliphatic compound with a melting point higher than room temperature, more preferably an aliphatic compound with a melting point of 40° C. or more, furthermore preferably an aliphatic compound with a melting point of 50° C. or more, and still furthermore preferably an aliphatic compound with a melting point of 55° C. or more. The melting point of such aliphatic compound is preferably 50-80° C., more preferably 50-70° C., furthermore preferably 55-70° C., and still furthermore preferably 55-65° C. The adhesive forces at the time of the application and re-application of a patch preparation to the skin can be adjusted depending on the melting point.

Examples of the aliphatic compound include $C_{8-22}$ higher alcohol and $C_{8-22}$ higher fatty acid, but are not limited thereto. In the present invention, $C_{8-22}$ higher alcohol and $C_{8-22}$ higher fatty acid may be used in combination.

As used herein, the term "in solid state at room temperature" means that the aliphatic compound is in solid state at about 25° C. and has no liquidity at about 25° C. The aliphatic compound in the state comprises a semi-solid solvent like petrolatum jelly. The aliphatic compound in the state is preferably in solid state. The aliphatic compound is particularly preferably an aliphatic compound dissolved in the solvent with a vapor pressure of 1 kPa or more at 20° C. mentioned below.

Examples of the $C_{8-22}$ higher alcohol may include octyl dodecanol, isostearyl alcohol, stearyl alcohol, lauryl alcohol, cetyl alcohol, palmityl alcohol, cetostearyl alcohol, decyl tetradecanol, hexyl decanol, behenyl alcohol, lauryl alcohol, and myristyl alcohol.

Examples of the $C_{8-22}$ higher fatty acid may include lauric acid, myristic acid, palmitic acid, and stearic acid. The aliphatic compound with hydrophilic group which is in solid state at room temperature is preferably $C_{8-22}$ higher alcohol, more preferably $C_{12-20}$ higher alcohol, furthermore preferably C$_{16-18}$ higher alcohol, still furthermore preferably stearyl alcohol, cetyl alcohol, or cetostearyl alcohol, and particularly preferably stearyl alcohol.

The amount of the aliphatic compound with hydrophilic group which is in solid state at room temperature is preferably 1-30% by weight, more preferably 2-25% by weight, furthermore preferably 2-20% by weight, still furthermore preferably 2-10% by weight, particularly preferably 2-5% by weight, and particularly more preferably 2-4% by weight, relative to the total weight of the plaster.

The aliphatic compound with hydrophilic group which is in solid state at room temperature may be combined with a drug. When oxycodone is used as the drug, the amount of the aliphatic compound with hydrophilic group which is in solid state at room temperature is more preferably 2-25% by weight, furthermore preferably 2-20% by weight, still furthermore preferably 2-10% by weight, particularly preferably 2-5% by weight, and particularly more preferably 2-4% by weight.

When fentanyl is used as the drug, the amount of the aliphatic compound with hydrophilic group which is in solid state at room temperature is more preferably 1-20% by weight, furthermore preferably 1-10% by weight, still furthermore preferably 1-5% by weight, particularly preferably 1-3% by weight, and particularly more preferably 1-2% by weight.

In addition, when oxycodone is used as the drug, the weight ratio of the aliphatic compound with hydrophilic group which is in solid state at room temperature and oxycodone is preferably 5:1-1:5, and more preferably 2:1-1:2. In order to calculate the weight ratio, oxycodone is used as hydrochloride thereof.

When fentanyl is used as the drug, the weight ratio of the aliphatic compound with hydrophilic group which is in solid state at room temperature and fentanyl is preferably 1:1-1:10, and more preferably 1:3-1:5.

[Non-Aqueous Adhesive]

The non-aqueous adhesive comprises a mass base and optionally a tackifier. The amount of the non-aqueous adhesive is, for example, 40-90% by weight, preferably 50-80% by weight, and more preferably 60-80% by weight relative to the total weight of the plaster.

The mass base may comprise a polymer. In one embodiment, the mass base comprises a polymer with rubber elasticity. Examples of the polymer may include an acrylic polymer, a rubber polymer, and a silicone polymer.

Specific examples of the rubber polymer include a synthetic rubber such as styrene-isoprene-styrene block copolymer (hereinafter also referred to as "SIS"), styrene-butadiene-styrene block copolymer, styrene-ethylene-butadiene rubber-styrene block copolymer, styrene-butadiene rubber, polyisoprene, polyisobutylene, polybutene, butyl rubber, silicone rubber; and natural rubber.

Specific examples of the acrylic polymer include polymethyl acrylate and polymethyl methacrylate. Examples thereof include DURO-TAK 87-2097, 87-2194, 87-2196, 87-2287, 87-2516, 87-2852, and 87-235A (Trade name, manufactured by Henkel Japan Ltd.), and NISSETSU KP-77, AS-370 (Trade name, manufactured by Nippon Carbide Industries Co., Inc.).

Specific examples of the silicone polymer include dimethylpolysiloxane and diphenylpolysiloxane.

The mass base as used herein preferably comprises an acrylic polymer. The acrylic polymer in the patch preparation of the present invention provides high adhesive force in the solvent-containing state. On the other hand, when a patch preparation comprising the acrylic polymer is re-applied to a human body, the acrylic polymer reduces the adhesive force of the patch preparation because of less compatibility with the aliphatic compound contained. As a result, it is thought that the patch preparation is capable of achieving both the high adhesiveness and the effect which makes it impossible to re-apply the patch preparation to the skin.

In the present invention, when the acrylic polymer is used as main mass base, that is, the acrylic polymer is used in an amount of more than 80% by weight relative to the total weight of the mass base, the amount of the aliphatic compound with hydrophilic group which is in solid state at room temperature is, for example, 5-30% by weight, preferably 5-25% by weight, more preferably 10-25% by weight, furthermore preferably 12-24% by weight, still furthermore preferably 15-24% by weight, particularly preferably 16-22% by weight, and particularly more preferably 18-20% by weight, relative to the total weight of the plaster.

The mass base as used herein preferably further comprises a rubber polymer. The mass base is more preferably a combination of a rubber polymer and an acrylic polymer. The weight ratio of the rubber polymer and the acrylic polymer (rubber polymer:rubber polymer) is preferably 5:1-1:5, more preferably 4:1-1:4, furthermore preferably 3:1-1:4, still furthermore preferably 2:1-1:4, particularly preferably 1:1-1:4, and particularly more preferably 1:2-1:3.

In this embodiment, the amount of the aliphatic compound with hydrophilic group which is in solid state at room temperature is preferably 1-5% by weight, more preferably 1-4% by weight, furthermore preferably 1-3% by weight, still furthermore preferably 1.5-3% by weight, and particularly preferably 2-2.5% by weight.

Examples of the tackifier may include alicyclic hydrocarbon resin, polyterpene resin, aliphatic hydrocarbon resin, polystyrene resin, rosin, and hydrogenated rosin. The tackifier is preferably terpene resin, that is, polyterpene resin. The amount of the tackifier is preferably 10-80% by weight, more preferably 20-70% by weight, furthermore preferably 30-60% by weight, still furthermore preferably 40-50% by weight, and particularly preferably 40-45% by weight.

The solvent with a vapor pressure of 1 kPa or more at 20° C. is preferably a solvent for dissolving the above aliphatic compound with hydrophilic group which is in solid state at room temperature, but is not limited thereto. In particular, it is preferable that the solution of the aliphatic compound in the solvent becomes clear. The above aliphatic compound and the solvent with a vapor pressure of 1 kPa or more at 20° C. are preferably used as a combination thereof with high miscibility.

Specific examples of the solvent with a vapor pressure of 1 kPa or more at 20° C. may include a non-cyclic or cyclic aliphatic hydrocarbon such as n-hexane, n-heptane, cyclohexane; an aliphatic monoalcohol such as ethanol, isopropyl alcohol, isobutyl alcohol, 2-butanol; an ester such as isobutyl acetate, isopropyl acetate, ethyl acetate; a ketone such as acetone, methyl ethyl ketone, methyl isobutyl ketone; an ether such as diethyl ether, tetrahydrofuran, 1,4-dioxane; an aromatic hydrocarbon such as benzene, xylene; an inorganic solvent such as water. The solvent may be used alone or two or more the solvents may be used in combination. Preferably, two or more the solvents are used in combination. The solvent with a vapor pressure of 1 kPa or more at 20° C. is preferably a non-cyclic or cyclic aliphatic hydrocarbon, an ester, water, or a combination thereof. In particular, a non-cyclic or cyclic aliphatic hydrocarbon and/or an ester are preferable, and a combination of a non-cyclic aliphatic hydrocarbon and an ester are more preferable. Specifically, ethyl acetate and/or n-heptane are preferable, and the combination of ethyl acetate and n-heptane is more preferable.

The solvent with a vapor pressure of 1 kPa or more at 20° C. is rapidly evaporated from the plaster at room temperature (about 25° C.) or skin surface temperature (about 32° C.), and thus the adhesive force of the plaster is reduced or lost. As a result, unexpected accidents due to the re-application of the patch preparation after use to the skin can be prevented. When the plaster comprises a drug, it is also expected that the skin permeability of the drug is reduced depending on the decreased amount of the solvent for dissolving the drug.

The amount of the solvent with a vapor pressure of 1 kPa or more at 20° C. is 2-35% by weight relative to the total weight of the plaster. When the amount of the solvent with a vapor pressure of 1 kPa or more at 20° C. does not satisfy the above range, the desired effect for reducing the adhesive force of the patch preparation may not be produced. Also, when the amount of the solvent exceeds the above range, the patch preparation may not be manufactured appropriately. Such range is not preferable.

In some embodiments, the amount of the solvent with a vapor pressure of 1 kPa or more at 20° C. is preferably 3-20% by weight, and more preferably 3-10% by weight.

In particular, when the plaster comprises a drug, the amount of the solvent with a vapor pressure of 1 kPa or more at 20° C. is preferably 5-25% by weight, more preferably 10-20% by weight, and furthermore preferably 15-18% by weight, relative to the total weight of the plaster.

When the plaster comprises a drug, the solvent with a vapor pressure of 1 kPa or more at 20° C. is preferably a solvent for dissolving the drug and enhancing the skin permeability of the drug.

When oxycodone is used as the drug, the solvent with a vapor pressure of 1 kPa or more at 20° C. is preferably a non-cyclic aliphatic hydrocarbon, an ester or a combination thereof, more preferably a combination of a non-cyclic aliphatic hydrocarbon and an ester, and furthermore preferably ethyl acetate and/or n-heptane. When a non-cyclic aliphatic hydrocarbon and an ester are used in combination, the weight ratio thereof is preferably 1:2-10:1, and more preferably 2:1-5:1. When ethyl acetate and n-heptane are used in combination, the weight ratio thereof is similar to the ratio described above. For example, the weight ratio of ethyl acetate:n-heptane may be selected from the range of 1:2-10:1.

When fentanyl is used as the drug, the solvent with a vapor pressure of 1 kPa or more at 20° C. may use ethanol, isopropanol, and ethyl acetate. The solvent is preferably a non-cyclic aliphatic hydrocarbon and/or an ester, more preferably a combination of a non-cyclic aliphatic hydrocarbon and an ester, and furthermore preferably ethyl acetate and/or n-heptane. When a non-cyclic aliphatic hydrocarbon and an ester are used in combination, the weight ratio thereof is preferably 1:2-10:1, and more preferably 1:1-4:1.

When the plaster does not comprise a drug, the amount of the solvent with a vapor pressure of 1 kPa or more at 20° C. is preferably 2-15% by weight, more preferably 5-15% by weight, and furthermore preferably 7-10% by weight, relative to the total weight of the plaster.

In some embodiments, the amount of the solvent with a vapor pressure of 1 kPa or more at 20° C. is 2-15% by weight relative to the total weight of the plaster.

The amount of the solvent with a vapor pressure of 1 kPa or more at 20° C. means the amount just before the patch preparation is applied to the skin. The amount of the solvent from the end of the preparation process to just before the patch preparation is applied to the skin is basically kept in a predetermined range by any means such as packaging the patch preparation with a suitable packaging material, as appropriate. Also, the surface of the plaster (the side opposite to the support) is typically protected by the removal-treated solvent-impermeable release film (liner). That is, the amount of the solvent with a vapor pressure of 1 kPa or more at 20° C. means not the charged amount but the amount just before the application to the skin represented as the amount after the coating and drying process of the plaster is terminated.

[Transdermal Absorptive Accelerator]

The plaster may further comprise an organic solvent with a vapor pressure of less than 1 kPa at 20° C. which can produce the transdermal absorption accelerating effect such as a fatty acid, an alcohol, an ester, and an organic amine. Specific examples of the fatty acid may include capric acid, sorbic acid, levulinic acid, and oleic acid; specific examples of the alcohol may include monohydric a higher alcohol such as capryl alcohol and oleyl alcohol, and a polyhydric alcohol such as propylene glycol, polyethylene glycol, and glycerin; specific examples of the ester may include propylene carbonate, diethyl sebacate, isopropyl myristate, diisopropyl adipate, myristyl palmitate, stearyl stearate, and medium-chain fatty acid triglyceride; and specific examples of the organic amine may include monoethanolamine, monoisopropanolamine, diethanolamine, diisopropanolamine, triethanolamine, and triisopropanolamine.

[Drug]

The patch preparation of the present invention may comprise a drug in the plaster. The drug may be selected from various drugs such as a hypnotic and sedative agent, a stimulant, a psychoneurotic agent, a local anesthetic, a muscle relaxant sucametonium, an antiparkinsonian agent, an antimigraine agent, an anti-smoking agent, an anti-allergic agent, an anti-Alzheimer's agent, and an opioid analgesic agent, but is not limited thereto. In the present invention, especially high child resistance is required. Hence, the drug is preferably an opioid analgesic agent such as morphine, codeine, fentanyl, oxycodone, and hydromorphone. In particular, the drug is more preferably fentanyl or oxycodone.

[Additive]

The plaster may further comprise one or more additives. The plaster preferably comprises an agent for preventing accidental ingestion. Examples of the agent may include a substance with strong bitter taste such as denatonium, preferably denatonium benzoate. The amount of the agent is preferably 0.01-0.1% relative to the total weight of the plaster. When the agent is denatonium benzoate, the amount thereof is preferably about 0.01-0.1% relative to the total weight of the plaster. The patch preparation comprising the agent in such amount produces strong bitter taste in mouth to exert the effect for preventing the accidental ingestion for people such as children.

Examples of the additive in the plaster include an additive which is well known and commonly used in the formulation field such as a filler, a softening agent, an antioxidant, a pH adjuster, and a flavoring agent.

[Support]

The patch preparation of the present invention comprises the plaster disposed on the support which is permeable to the solvent with a vapor pressure of 1 kPa or more at 20° C. (hereinafter, referred to as "solvent-permeable support"), or the support which is impermeable to the solvent with a vapor pressure of 1 kPa or more at 20° C. (hereinafter, referred to as "solvent-impermeable support"). Examples of the solvent-permeable support may include woven or non-woven cloth and porous sheet which comprises a material such as a resin (e.g., polyester, polypropylene, polyurethane, and vinyl chloride) and pulp. Examples of the solvent-impermeable support may include a film comprising a resin such as PET (polyethylene terephthalate), polyamide, and vinyl chloride, and a film comprising woven or non-woven cloth coated with a resin such as PET.

The multi-layered patch preparation comprising the plaster disposed on the solvent-permeable support of the present invention can prevent the evaporation of the solvent from the plaster by any means such as packaging the patch preparation with a suitable packaging material until the patch preparation is applied to the skin. Examples of the packaging material include film bag, and the film moiety thereof is preferably multi-layered film. The multi-layered film can easily reduce the permeability of a solvent. In particular, the film moiety thereof is preferably aluminum laminated film. Examples of the preferred material for the innermost layer include polyethylene and PET. The amount of the solvent with a vapor pressure of 1 kPa or more at 20° C. is kept in a predetermined amount until the patch preparation is applied to the skin. The adhesive force of the plaster under this condition is sufficient, and thus the plaster is attached to the skin and the attached state between the plaster and the skin is kept. During the adhesion to the skin, the solvent with a vapor pressure of 1 kPa or more at 20° C. is evaporated from the plaster through the solvent-permeable support. Even if the solvent with a vapor pressure of 1 kPa or more at 20° C. is evaporated, the patch preparation can keep the state attached to the skin. On the other hand, when the patch preparation in the state that the solvent with a vapor pressure of 1 kPa or more at 20° C. has been evaporated from the plaster is removed from the skin, the patch preparation is not re-attached to the skin because of the loss or reduction of the adhesive force of the plaster. As used herein, the term "the state the solvent with a vapor pressure of 1 kPa or more at 20° C. has been evaporated from the plaster means that the amount of the solvent with a vapor pressure of 1 kPa or more at 20° C. reaches less than 50% or less than 75% of the solvent until the patch preparation is applied to the skin.

The multi-layered patch preparation comprising the plaster disposed on the solvent-impermeable support of the present invention can prevent the evaporation of the solvent from the plaster by any means such as packaging the patch preparation with a suitable packaging material until the patch preparation is applied to the skin. Examples of the packaging material include film bag, and the film moiety thereof is preferably multi-layered film. The multi-layered film can easily reduce the permeability of a solvent. In particular, the film moiety thereof is preferably aluminum laminated film. Examples of the preferred material for the innermost layer include polyethylene and PET. The amount of the solvent with a vapor pressure of 1 kPa or more at 20° C. in the plaster is kept in a predetermined amount until the patch preparation is applied to the skin. Also, the amount of the solvent is not substantially changed even after the patch preparation is applied to the skin, because the plaster is located between the solvent-impermeable support and the skin. However, the plaster is warmed by body temperature, and the plaster temperature reaches around skin surface temperature (about 32° C.). Hence, the solvent with a vapor pressure of 1 kPa or more at 20° C. in the plaster is rapidly evaporated after the plaster is removed from the skin. As a result, the adhesive force of the plaster is reduced or lost, and thus the plaster cannot be re-attached to the skin. Also, when the plaster comprises a drug dissolved in a solvent with a vapor pressure of 1 kPa or more at 20° C., the drug hardly permeates the skin even if the plaster is attached to the skin, because the solvent is evaporated from the plaster.

In the patch preparation of the present invention, the solvent-permeable and solvent-impermeable supports may be used in combination. The patch preparation can form a multi-layered preparation comprising the first and second plasters, and the first and second supports. For example, the first support may be a solvent-impermeable support, and the second support may be a solvent-permeable support. When the patch preparation is such multi-layered preparation, the structure comprising the first plaster comprising no drug and the second plaster comprising a drug is preferable. The first support, the first plaster, the second support, and the second plaster are sequentially laminated toward the adhesion to the skin from the support side of the patch preparation. The surface areas of the first plaster, second support and second plaster satisfy the following formula:

first plaster>second support≥second plaster.

Particularly preferably, the surface areas of the supports and plasters satisfy the following formula:

first support≥first plaster>second support≥second plaster.

The first plaster plays a role in applying the patch preparation to the skin, and the second plaster plays a role in releasing a drug contained therein after applying the patch preparation to the skin. The surface area of the first plaster is preferably larger as compared to those of the second support and the second plaster. The surface area of the second support is preferably less than 90%, more preferably less than 80%, furthermore preferably less than 50%, and particularly preferably less than 30%, relative to that of the first plaster. In order to keep the adhesive force of the patch preparation and effectively release a drug in the plaster, the surface area of the second support is preferably 20% or more and less than 90%, and more preferably 50% or more and less than 80%.

Also, considering the adhesive force and ease of use, the average distance to the outer edge of the first plaster protruding from the second support when the geometric center of the second support is superposed with that of the first plaster is preferably 4-20 mm, more preferably 5-16 mm, and furthermore preferably 6-15 mm.

The second plaster is not particularly required to have adhesive force. The second plaster preferably has no adhesive force capable of keeping the adhesion to the skin.

In addition, the first and second supports may independently be a solvent-impermeable support or a solvent-permeable support. The supports are preferably a solvent-permeable support. The solvent-impermeable support is preferably resin film, more preferably polyester film, and furthermore preferably PET film. In particular, the solvent-impermeable support is preferably non-woven cloth laminated film, and more preferably non-woven cloth laminated PET film. When the second support is solvent-impermeable support, the second support is preferably non-woven cloth laminated film. The non-woven cloth moiety thereof is preferably disposed on the second plaster. In some embodiments, the second plaster may be held on the concavo-convex moiety of the non-woven cloth to apply a drug to a desired site. Also, the adhesive force of the second support can be enhanced by disposing the flat and smooth film surface on the first plaster. As a result, the removal of the second support from the first plaster can be prevented.

The first support is more preferably non-woven cloth laminated PET film. The film moiety thereof is preferably disposed on the first plaster. The adhesive force of the first support can be enhanced by disposing the flat and smooth film surface on the first plaster. As a result, the removal of the first support from the first plaster can be prevented. The non-woven cloth moiety of the first support is located outside, and thus the first plaster can reduce the differences in the feeling with the surrounding skin and the shape and produce an excellent usability.

As described above, the first plaster has adhesive force when the plaster is applied to the skin and keep the adhesion to the skin thereafter. On the other hand, the solvent with a vapor pressure of 1 kPa or more at 20° C. is evaporated from the plaster while the plaster is applied to the skin. As a result, the adhesive force of the plaster is lost when the plaster is removed from the skin, and the plaster cannot be re-attached to the skin.

The second plaster comprises a drug dissolved in a solvent with a vapor pressure of 1 kPa or more at 20° C. while the plaster is applied to the skin, and thus the drug can permeate the skin. On the other hand, when the second plaster is removed from the skin, the solvent therein is rapidly evaporated. As a result, when the second plaster is re-attached to the skin, the skin permeability of the drug is greatly reduced.

Accordingly, in the multi-layered patch preparation of the present invention, the first plaster preferably comprises the solvent with a vapor pressure of 1 kPa or more at 20° C. in an amount of 2-35% by weight, and the first and second plasters preferably comprise the solvent with a vapor pressure of 1 kPa or more at 20° C. in an amount of 2-35% by weight.

The amount of the solvent with a vapor pressure of 1 kPa or more at 20° C. in the first plaster is preferably 2-15% by weight, more preferably 5-15% by weight, and furthermore preferably 7-10% by weight, relative to the total weight of the plaster.

Also, the amount of the solvent with a vapor pressure of 1 kPa or more at 20° C. in the second plaster is preferably 5-25% by weight, more preferably 10-20% by weight, and furthermore preferably 15-18% by weight, relative to the total weight of the plaster.

[Preparation Process of Patch Preparation]

The preparation process of the patch preparation of the present invention comprises the step of mixing an aliphatic compound with hydrophilic group which is in solid form at room temperature, a non-aqueous adhesive, and a solvent with a vapor pressure of 1 kPa or more at 20° C. to give the mixture, and coating the mixture onto a support and drying.

Specifically, a solvent with a vapor pressure of 1 kPa or more at 20° C. in an amount of more than the given amount (necessary amount), an aliphatic compound, a non-aqueous adhesive, and optionally an additive are added and mixed to prepare a coating solution. The coating solution is coated on release film or a support and dried. The excess amount of the solvent added is evaporated, and then a plaster is laminated onto the support or release film. Preferably, the plaster temperature is increased to 50° C. or more after drying or after the plaster is laminated onto the support or release film.

According to the process, the patch preparation comprising the plaster comprising the aliphatic compound, the non-aqueous adhesive, and the solvent with a vapor pressure of 1 kPa or more at 20° C. in a given amount. The patch preparation preferably comprises the solvent with a vapor pressure of 1 kPa or more at 20° C. in an amount of 2-35% by weight.

In more preferable embodiments, the multi-layered patch preparation of the present invention can be also prepared in a similar process to the above process. The patch preparation of the present invention preferably comprises a first plaster comprising no drug and a second plaster comprising a drug. The amount of the solvent with a vapor pressure of 1 kPa or more at 20° C. in each plaster is preferably 2-35% by weight relative to the total weight of the plaster. In particular, the amount of the solvent in the first plaster is preferably 2-15% by weight relative to the total weight of the plaster, and the amount of the solvent in the second plaster is 5-25% by weight relative to the total weight of the plaster. The amount of each solvent in the plasters is more preferably the amount described in the above paragraph describing the amount of the solvent in each plaster.

The patch preparation thus prepared is laminated each other to prepare multi-layered patch preparation. The prepared patch preparation is packaged with a suitable packaging material. Examples of the packaging material include film bag, and the film moiety thereof is preferably multi-layered film, and more preferably aluminum laminated film. Examples of the preferred material for the innermost layer include polyethylene and PET.

Two or more solvents with a vapor pressure of 1 kPa or more at 20° C. are added in excess amounts at a ratio according to the vapor pressure at the time of drying or evaporation process and dried. The process for drying the solvents may be terminated when the excess amount of the solvents reaches a desired amount to adjust the amount of the solvents. In order to adjust the amount of the solvents more accurately, the amount of the solvents in the prepared patch preparation may be quantified by gas chromatography or liquid chromatography to adjust the excess amount thereof.

EXAMPLES

Hereinafter, the present invention is described more specifically with reference to Examples. However, the present invention is not intended to be limited to them by any means.

The patch preparations of Examples 1-5 and Comparative Example 1 with the compositions shown in Table 1 below were prepared as follows.

The ingredients shown in Table 1 were weighted. Ethyl acetate and heptane were added more than the given amounts, and the ingredients were mixed to prepare a coating solution. The coating solution was coated on the silicone-treated PET film (release liner) and dried, and the solvents in the excess amounts were evaporated. The plaster was then laminated onto the PET film moiety of non-woven cloth laminated PET film (support) at 70° C. to prepare the patch preparations of Examples 1-5 and Comparative Example 1. Each of the prepared patch preparations was placed in aluminum laminated bag and sealed.

In addition, in each patch preparation, the release liner was removed to expose the plaster, and the exposed plaster was placed at room temperature for 30 minutes. The adhesive force of each patch preparation after the preparation was placed for 0 minute and 30 minutes was measured by touching the plaster with a hand. The re-adhesiveness of each patch preparation was then measured by applying the patch preparation to forearm. The results are shown in Table 1.

TABLE 1

| | | | Example 1 | Example 2 | Example 3 | Example 4 | Example 5 | Comparative Example 1 |
|---|---|---|---|---|---|---|---|---|
| Plaster 1 | Aliphatic Compound | Steary Alcohol (mp 59.8° C.) | 2.3 | 19 | 2.21 | | | |
| | | Stearic Acid (mp 69.6° C.) | | | | 2.21 | | |
| | | Myristic Acid (mp 54.4° C.) | | | | | 2.21 | |
| | Adhesive | SIS | 15.1 | | 16.92 | 16.92 | 16.92 | 16.92 |
| | | Terpene Resin | 37.8 | | 34.57 | 34.57 | 34.57 | 34.57 |
| | | Acrylic resin | 37.8 | 76 | 36.77 | 36.77 | 36.77 | 36.77 |
| | Solvent | Ethyl Acetate | 1.5 | 3 | 3.00 | 3.00 | 3.00 | 3.00 |
| | | Heptane | 5.5 | 2 | 6.00 | 6.00 | 6.00 | 6.00 |
| | | Water | | | 0.37 | 0.37 | 0.37 | 0.37 |
| | Additive | Propyl Gallate | | | 0.05 | 0.05 | 0.05 | 0.05 |
| | | Denatonium Benzoate | | | 0.01 | 0.01 | 0.01 | 0.01 |
| | | Sodium Metabisulfite | | | 0.10 | 0.10 | 0.10 | 0.10 |
| | | Total | 100 | 100 | 100.00 | 100.00 | 100.00 | 97.79 |
| Support 1 | | | Non-woven cloth laminated PET film (Plaster moiety is PET film) | Non-woven cloth laminated PET film (Plaster moiety is PET film) | Non-woven cloth laminated PET film (Plaster moiety is PET film) | Non-woven cloth laminated PET film (Plaster moiety is PET film) | Non-woven cloth laminated PET film (Plaster moiety is PET film) | Non-woven cloth laminated PET film (Plaster moiety is PET film) |
| Adhesiveness | 0 minute | | Adhesion | Adhesion | Adhesion | Adhesion | Adhesion | Adhesion |
| | 30 minutes | | No adhesion | No adhesion | No adhesion | No adhesion | The patch preparation is removed from the skin after adhesion | No adhesion |

As shown in Table 1, it was found that the preparations of Examples 1-5 and Comparative Example 1 had adhesive force at 0 minute after placing, and were not removed from the applied forearm. At 30 minutes after placing, the preparations of Examples 1-4 did not have adhesive force and could not apply them to the forearm. The patch preparation of Example 5 had slight adhesive force at 30 minutes after placing, but were removed from the applied forearm. On the other hand, the preparation of Comparative Example 1 had adhesive force at 30 minutes after placing and was not removed from the applied forearm.

It was demonstrated that the use of the aliphatic compound with hydrophilic group which is in solid state at room temperature reduced the adhesiveness of the re-applied patch preparation. As a result, it was suggested that the patch preparation comprising the aliphatic compound of the present invention could produce the effect which made it impossible to re-apply the patch preparation to the skin.

The patch preparations of Examples 6-7 and Comparative Example 2 with the compositions shown in Table 2 below were prepared as follows.

The ingredients shown in Table 2 were weighted. Ethyl acetate and heptane were added more than the given amounts, and the ingredients were mixed to prepare a coating solution. The coating solution was coated on the silicone-treated PET film (release liner) and dried, and the excess amounts of the solvents added were evaporated. The plaster 2 was then laminated onto the non-woven cloth moiety of non-woven cloth laminated PET film (support 2) at 70° C. to prepare the patch preparations comprising the plaster 2 and the support 2 of Examples 6-7 and Comparative Example 2. The plaster 2 of the patch preparations of Examples 6-7 and the plaster 2 of the patch preparation of Comparative Example 2 were then laminated onto the plaster 1 of the patch preparation of Example 3 and the plaster 1 of the patch preparation of Comparative 1, respectively. The release liner on the plaster 2 moiety of each patch preparation was removed, and the plaster 1 was laminated onto the silicone-treated PET film (release liner) so that the plaster 1 is covered to prepare each multi-layered preparation. Each of the prepared patch preparations was placed in aluminum laminated bag and sealed.

In addition, in each patch preparation, the release liner was removed to expose the plaster, and the exposed plaster was placed at room temperature for 30 minutes. The adhesive force of each patch preparation after the preparation was placed for 0 minute and 30 minutes was measured by touching the plaster with a hand. The re-adhesiveness of each patch preparation was then measured by applying the patch preparation to forearm. The results are shown in Table 2.

TABLE 2

| | | | Example 6 | Example 7 | Comparative Example 2 |
|---|---|---|---|---|---|
| Plaster 2 | Aliphatic Compound | Steary Alcohol | 3.65 | 1.65 | |

TABLE 2-continued

|  |  |  | Example 6 | Example 7 | Comparative Example 2 |
|---|---|---|---|---|---|
|  | Adhesive | Styrene-Isoprene-Styrene Block Copolymer | 28.14 | 45.28 | 28.14 |
|  |  | Terpene Resin | 21.89 | 9.07 | 21.89 |
|  |  | Acrylic resin | 9.74 | 19.78 | 9.74 |
|  | Solvent | Ethyl Acetate | 5.00 | 5.80 | 5.00 |
|  |  | Heptane | 12.00 | 11.70 | 12.00 |
|  | Drug | Oxycodone HCl | 3.13 |  | 3.13 |
|  |  | Fentanyl |  | 6.59 |  |
|  | Transdermal Absorptive Accelerator | Oleic Acid | 4.17 |  | 4.17 |
|  |  | Diisopropanolamine | 1.19 |  | 1.19 |
|  |  | Propylene Carbonate | 5.21 |  | 5.21 |
|  |  | Glycerin | 2.61 |  |  |
|  | Additive | Propyl Gallate | 0.05 | 0.04 | 0.05 |
|  |  | Denatonium Benzoate | 0.01 | 0.01 | 0.01 |
|  |  | Sodium Metabisulfite | 0.10 |  | 0.10 |
|  |  | Sodium Sulfite |  | 0.08 |  |
|  |  | Light Anhydrous Silicic Acid | 3.13 |  | 3.13 |
|  |  | Total | 100.00 | 100.00 | 96.35 |
| Support 2 |  | Non-woven cloth laminated PET film (Plaster 2 side is on-woven cloth) |  |  |  |
| Plaster 1 |  |  | Example 3 | Example 3 | Comparative Example 1 |
| Support 1 |  |  | Example 3 | Example 3 | Comparative Example 1 |
| Adhesiveness | 0 minute |  | Adhesion | Adhesion | Adhesion |
|  | 30 minutes |  | No adhesion | No adhesion | Adhesion |

As shown in Table 2, it was found that the preparations of Examples 6-7 and Comparative Example 2 had adhesive force at 0 minute after placing, and were not removed from the applied forearm. At 30 minutes after placing, the preparations of Examples 6-7 did not have adhesive force and could not apply them to the forearm. On the other hand, the preparation of Comparative Example 2 had adhesive force at 30 minutes after placing, and were not removed from the applied forearm.

Test for Evaluating Adhesive Force of Patch Preparation after Re-Application to the Skin The adhesive force of each preparation of Examples 8-10 and Comparative Example 2 prepared in a similar process to that of Example 1 after the re-application to the skin was evaluated according to "The Japanese Pharmacopoeia, Seventeenth Edition, General Tests, 6.12 Methods of Adhesion Testing, 3.3 Rolling ball tack testing". Specifically, each preparation after the plaster was exposed by the removal of the release liner (length: 150 mm) was secured on the lower position of the ball-rolling device with an inclination angle of 21.5 degrees, No. 14 balls with a diameter of 7/16 inch for adhesion testing was rolled down from the upper position of the device, and the distance when the ball stopped on the adhesive face (mm) was measured. Next, each distance when the ball stopped on the adhesive face (mm) after placing at room temperature for 15 and 30 minutes was measured. The results are shown in Table 3.

The adhesive force of the patch preparation after placing for 0 minute was defined as "initial adhesive force". The smaller value shows that the patch preparation has higher adhesive force, and the larger value shows that the patch preparation has lower adhesive force.

TABLE 3

|  |  |  | Example 8 | Example 9 | Example 10 | Comparative Example 2 |
|---|---|---|---|---|---|---|
| Plaster | Aliphatic Compound | Steary Alcohol (mp 59.8° C.) | 2.22 |  |  |  |
|  |  | Stearic Acid (mp 69.6° C.) |  | 2.22 |  |  |
|  |  | Myristic Acid (mp 54.4° C.) |  |  | 2.22 |  |
|  | Adhesive | SIS | 17.02 | 17.02 | 17.02 | 17.02 |
|  |  | Terpene Resin | 34.77 | 34.77 | 34.77 | 34.77 |
|  |  | Acrylic resin | 36.99 | 36.99 | 36.99 | 36.99 |
|  | Solvent | Ethyl Acetate | 3.00 | 3.00 | 3.00 | 3.00 |
|  |  | Heptane | 6.00 | 6.00 | 6.00 | 6.00 |
|  |  | Total | 100.00 | 100.00 | 100.00 | 97.78 |

TABLE 3-continued

|  |  | Example 8 | Example 9 | Example 10 | Comparative Example 2 |
|---|---|---|---|---|---|
| Support |  | Non-woven cloth laminated PET film (Plaster side is PET film) | Non-woven cloth laminated PET film (Plaster side is PET film) | Non-woven cloth laminated PET film (Plaster side is PET film) | Non-woven cloth laminated PET film (Plaster side is PET film) |
| Re-adhesiveness | 0 minute | 13.3 | 44.1 | 26.6 | 9.5 |
|  | 15 minutes | >150 | >150 | 48.4 | 33.2 |
|  | 30 minutes | >150 | >150 | 73.3 | 40.3 |

According to the results of Tables 2 and 3, it was shown that the patch preparation comprising stearyl alcohol as the aliphatic compound had the remarkable excellent effect which made it impossible to re-apply the patch preparation to the skin.

INDUSTRIAL APPLICABILITY

The present invention provides a patch preparation which can produce the effect for preventing any problems due to the misuse of the patch preparation.

The invention claimed is:

1. A patch preparation comprising a support and a plaster, wherein the plaster comprises a) an aliphatic compound with hydrophilic group which is in solid state at room temperature, b) a non-aqueous adhesive, and c) a solvent with a vapor pressure of 1 kPa or more at 20° C. in an amount of 15-35% by weight based on the plaster after drying the patch preparation but before applying the patch preparation.

2. The patch preparation of claim 1, wherein the support is a solvent-impermeable support.

3. The patch preparation of claim 1, wherein the support is a solvent-permeable support.

4. The patch preparation of claim 1, wherein the aliphatic compound is a compound with a melting point of 50-80° C.

5. The patch preparation of claim 1, wherein the aliphatic compound is one or more selected from the group consisting of $C_{8-22}$ higher alcohol and $C_{8-22}$ higher fatty acid.

6. The patch preparation of claim 1, wherein the aliphatic compound is one or more selected from the group consisting of stearyl alcohol, cetyl alcohol, cetostearyl alcohol, myristic acid, palmitic acid, and stearic acid.

7. The patch preparation of claim 1, wherein the non-aqueous adhesive comprises a mass base, and the mass base is an acrylic polymer or a combination of an acrylic polymer and a rubber polymer.

8. The patch preparation of claim 1, wherein the solvent is one or more selected from the group consisting of an acyclic or cyclic aliphatic hydrocarbon, an ester, and water.

9. The patch preparation of claim 1, wherein the solvent is ethyl acetate and n-heptane.

10. The patch preparation of claim 1, wherein the plaster further comprises a drug.

11. The patch preparation of claim 10, wherein the drug is an opioid analgesic agent.

12. The patch preparation of claim 11, wherein the opioid analgesic agent is oxycodone or fentanyl.

13. The patch preparation of claim 7, wherein the mass base is a combination of an acrylic polymer and a rubber polymer and the weight ratio of the acrylic polymer and rubber polymer is 2:1-1:4.

14. The patch preparation of claim 9, wherein the weight ratio of n-heptane and ethyl acetate is 1:1-4:1.

15. A patch preparation comprising a support and a plaster, wherein the plaster comprises a) a drug, b) an aliphatic compound with hydrophilic group which is in solid state at room temperature, c) a non-aqueous adhesive, and d) a solvent with a vapor pressure of 1 kPa or more at 20° C., wherein the drug is fentanyl and the aliphatic compound is stearyl alcohol, and wherein the amount of the solvent with a vapor pressure of 1 kPa or more at 20° C. is 15-35% by weight after drying the plaster.

16. The patch preparation of claim 15, wherein the amount of stearyl alcohol is 1-2% by weight.

17. The patch preparation of claim 15, wherein the solvent is ethyl acetate and n-heptane and the weight ratio of n-heptane and ethyl acetate is 1:1-4:1.

18. The patch preparation of claim 15, wherein the weight ratio of stearyl alcohol and fentanyl is 1:1-1:10.

19. The patch preparation of claim 18, wherein the solvent is ethyl acetate and n-heptane and the weight ratio of n-heptane and ethyl acetate is 1:1-4:1.

20. The patch preparation of claim 1, wherein the patch preparation excludes water as a solvent.

21. A patch preparation comprising a support and a plaster, wherein the plaster comprises a) an aliphatic compound with hydrophilic group which is in solid state at room temperature, b) a non-aqueous adhesive, and c) a solvent with a vapor pressure of 1 kPa or more at 20° C. in an amount of 15-35% by weight based on the plaster after coating and drying of the plaster on the support.

22. The patch preparation of claim 1, wherein the solvent is selected from the group consisting of acetone, ethanol, ethyl acetate, heptane, isopropanol, and methyl ethyl ketone.

* * * * *